US011775153B2

(12) United States Patent
Conrad et al.

(10) Patent No.: US 11,775,153 B2
(45) Date of Patent: Oct. 3, 2023

(54) ASSESSING MEASUREMENT ERRORS IN SOFTWARE CALCULATIONS

(71) Applicant: Fujifilm Medical Systems U.S.A., Inc., Lexington, MA (US)

(72) Inventors: Matthew Conrad, Raleigh, NC (US); Richard Cato, Hillsborough, NC (US); Mitchell Kobelinski, Raleigh, NC (US)

(73) Assignee: Fujifilm Medical Systems U.S.A., Inc., Morrisville, NC (US)

( * ) Notice: Subject to any disclaimer, the term of this patent is extended or adjusted under 35 U.S.C. 154(b) by 0 days.

(21) Appl. No.: 17/651,442

(22) Filed: Feb. 17, 2022

(65) Prior Publication Data

US 2023/0259259 A1    Aug. 17, 2023

(51) Int. Cl.
*G06F 3/04842* (2022.01)
*A61B 8/00* (2006.01)
*G06V 20/70* (2022.01)

(52) U.S. Cl.
CPC .......... *G06F 3/04842* (2013.01); *A61B 8/465* (2013.01); *A61B 8/468* (2013.01); *G06V 20/70* (2022.01)

(58) Field of Classification Search
CPC .............. G06F 3/048; G06F 3/04842; G06F 11/36–3696; G06V 20/70; G06T 11/20–206; G06T 2207/30004–30104; G06T 7/0012–0016; G06T 7/10–194; A61B 8/465; A61B 8/468
See application file for complete search history.

(56) References Cited

U.S. PATENT DOCUMENTS

| | | | | |
|---|---|---|---|---|
| 10,127,662 | B1* | 11/2018 | Reicher | ..................... G06T 7/30 |
| 2009/0290766 | A1* | 11/2009 | Salafia | ..................... G06T 7/41 |
| | | | | 382/128 |
| 2010/0293530 | A1* | 11/2010 | Ivancic | ............... G06F 11/3608 |
| | | | | 717/126 |

(Continued)

OTHER PUBLICATIONS

Philbrick, Kenneth A., et al. "RIL-contour: a medical imaging dataset annotation tool for and with deep learning." Journal of digital imaging 32.4 (2019): 571-581. (Year: 2019).*

*Primary Examiner* — Liang Y Li
(74) *Attorney, Agent, or Firm* — Heslin Rothenberg Farley & Mesiti P.C

(57) ABSTRACT

Examples herein include methods, systems, and computer program products for transparently determining the accuracy of image analysis and processing software where program code executing on a processor(s) determines that an image has been selected in a software of interest and is displayed in a viewer of the software of interest. The program code automatically launches a graphical user interface (window), on the screen, displayed contemporaneously with the viewer. The program code automatically annotates a region of the image in the window using an annotation defined by a specification. The program code calculates (using instructions from the specification) the first set of the values. The program code obtains a second set of the one or more values, calculated by the software, based on the annotation; The program code compares the value sets to identify discrepancies. The program code determines a reason for each discrepancy and displays the reason in the window.

20 Claims, 11 Drawing Sheets

(56) References Cited

U.S. PATENT DOCUMENTS

| | | | |
|---|---|---|---|
| 2015/0078643 A1* | 3/2015 | John | G06T 7/11 |
| | | | 382/131 |
| 2015/0086133 A1* | 3/2015 | Grady | G06T 7/97 |
| | | | 382/278 |
| 2017/0091582 A1* | 3/2017 | Takata | G16H 30/20 |
| 2018/0342060 A1* | 11/2018 | Yao | G16H 40/63 |
| 2020/0178845 A1* | 6/2020 | Castillo | A61B 5/091 |
| 2022/0071595 A1* | 3/2022 | Mienkina | G06F 3/0482 |
| 2022/0222952 A1* | 7/2022 | Luo | G06T 7/10 |

\* cited by examiner

ASSESSING MEASUREMENT ERRORS IN SOFTWARE CALCULATIONS

BACKGROUND

Various software products allow users to manipulate Digital Imaging and Communications in Medicine (DICOM) images. One such function is to isolate and annotate regions of interest (ROIs) in the displayed images. When isolating these ROIs, the accuracy of the calculations related to the sizing of the items isolated is important to diagnosis and treatment of maladies revealed in the images. However, many software products trade-off accuracy of calculations related to the ROIs to provide the user with speed and usability when working with the images. For example, various compression and sampling techniques are utilized in software to increase response time. An industry standard in calculations related to DICOM images in software is real-time, close to real-time, or, at most, seconds. Thus, compression techniques and shortcuts integrated into software to meets usability demands can compromise the accuracy of the calculations.

SUMMARY

Shortcomings of the prior art are overcome, and additional advantages are provided through the provision of a method for verifying medical imaging calculations. The method includes, for example: determining, by one or more processors, that an image has been selected in a software of interest and is displayed in a viewer of the software of interest, wherein the viewer is a graphical user interface of the software of interest in a screen communicatively coupled to the one or more processors; automatically launching, by the one or more processors, a graphical user interface comprising a window, on the screen, wherein the window is displayed on the screen contemporaneously with the viewer; automatically annotating, by the one or more processors, a region of the image in the window, wherein the annotating comprises an annotation defined by a specification document stored on a memory communicatively coupled to the one or more processors; obtaining, by the one or more processors, from the specification, instructions for calculating a set first of the one or more values based on the annotation defined by the specification; calculating, by the one or more processors, based on the instructions, the first set of the one or more values; obtaining, by the one or more processors, from the software of interest, a second set of the one or more values, wherein the second set of the one or more values were calculated by the software of interest based on the annotation; comparing, by the one or more processors, the first set of the one or more values to the second set of the one or more values to identify one or more discrepancies outside of a pre-defined tolerance; and based on identifying one or more discrepancies outside of the pre-defined tolerance, determining, by the one or more processors, a reason for each discrepancy of the one or more discrepancies, wherein the determining comprises displaying the reason for each discrepancy in the window.

Shortcomings of the prior art are overcome, and additional advantages are provided by a system that verifies the veracity of a medical image analysis system. The system includes: a memory; one or more processors in communication with the memory; and program instructions stored on the memory that when executed by the one or more processors cause the one or more processors to execute a method. The method can include: determining, by the one or more processors, that an image has been selected in a software of interest and is displayed in a viewer of the software of interest, wherein the viewer is a graphical user interface of the software of interest in a screen communicatively coupled to the one or more processors; automatically launching, by the one or more processors, a graphical user interface comprising a window, on the screen, wherein the window is displayed on the screen contemporaneously with the viewer; automatically annotating, by the one or more processors, a region of the image in the window, wherein the annotating comprises an annotation defined by a specification document stored on a memory communicatively coupled to the one or more processors; obtaining, by the one or more processors, from the specification, instructions for calculating a set first of the one or more values based on the annotation defined by the specification; calculating, by the one or more processors, based on the instructions, the first set of the one or more values; obtaining, by the one or more processors, from the software of interest, a second set of the one or more values, wherein the second set of the one or more values were calculated by the software of interest based on the annotation; comparing, by the one or more processors, the first set of the one or more values to the second set of the one or more values to identify one or more discrepancies outside of a pre-defined tolerance; and based on identifying one or more discrepancies outside of the pre-defined tolerance, determining, by the one or more processors, a reason for each discrepancy of the one or more discrepancies, wherein the determining comprises displaying the reason for each discrepancy in the window.

Additional features are realized through the devices and techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

Figure 1:
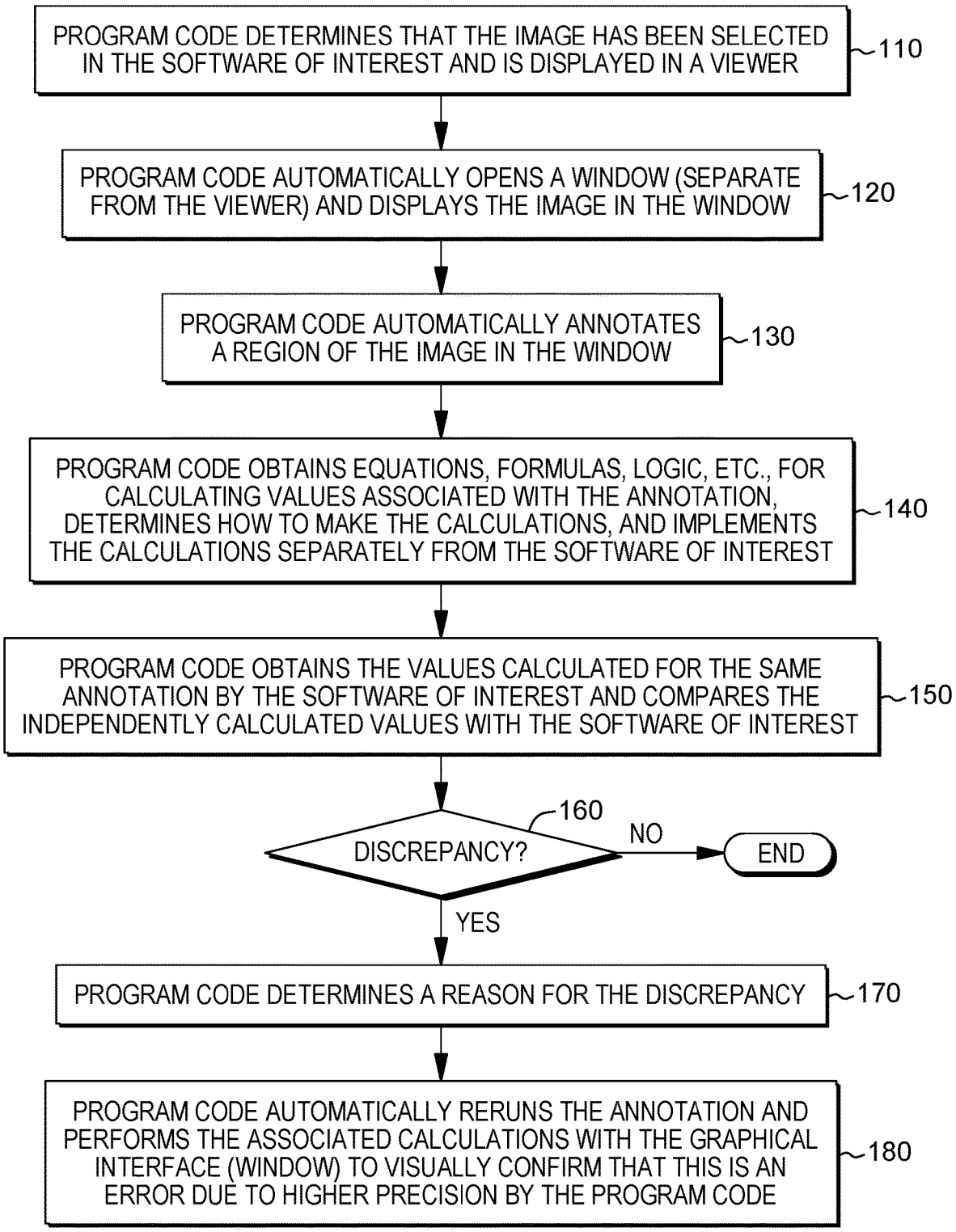
FIG. 1 is an example of a workflow that illustrates various aspects of some embodiments of the present invention.

The accompanying figures, which are not drawn to scale for ease of understanding, in which like reference numerals may refer to identical or functionally similar elements throughout the separate views and which are incorporated in and form a part of the specification, further illustrate the present invention and, together with the detailed description of the invention, serve to explain the principles of the present invention. As understood by one of skill in the art, the accompanying figures are provided for ease of understanding and illustrate aspects of certain embodiments of the present invention. The invention is not limited to the embodiments depicted in the figures.

The terms "connect," "connected," "contact" "coupled" and/or the like are broadly defined herein to encompass a variety of divergent arrangements and assembly techniques. These arrangements and techniques include, but are not limited to (1) the direct joining of one component and another component with no intervening components therebetween (e.g., the components are in direct physical contact); and (2) the joining of one component and another component with one or more components therebetween, provided that the one component being "connected to" or "contacting" or "coupled to" the other component is somehow in operative communication (e.g., electrically, fluidly, physically, optically, etc.) with the other component (notwithstanding the presence of one or more additional components therebetween). It is to be understood that some components that are in direct physical contact with one another may or may not be in electrical contact and/or fluid contact with one another. Moreover, two components that are electrically connected, electrically coupled, optically connected, optically coupled, fluidly connected or fluidly coupled may or may not be in direct physical contact, and one or more other components may be positioned therebetween.

The terms "including" and "comprising", as used herein, mean the same thing.

The terms "substantially", "approximately", "about", "relatively," or other such similar terms that may be used throughout this disclosure, including the claims, are used to describe and account for small fluctuations, such as due to variations in processing, from a reference or parameter. Such small fluctuations include a zero fluctuation from the reference or parameter as well. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. If used herein, the terms "substantially", "approximately", "about", "relatively," or other such similar terms may also refer to no fluctuations.

As used herein, "electrically coupled" refers to a transfer of electrical energy between any combination of a power source, an electrode, a conductive surface, a droplet, a conductive trace, wire, waveguide, nanostructures, other circuit segment and the like. The terms electrically coupled may be utilized in connection with direct or indirect connections and may pass through various intermediaries, such as a fluid intermediary, an air gap and the like.

As used herein, the term Digital Imaging and Communications in Medicine (DICOM) images refers to images whose structure organization of the information related to the communication of medical images is defined by the DICOM Information Model. Within the DICOM Information Model, a service-object pair (SOP) class defines the rules and semantics to communicate an image between two systems. The SOP class utilized to transmit and store an image is dependent upon the type of image transmitted and the intended response of the destination system. Within the DICOM Information Model, an information object definition (IOD) is an abstract data model used to specify information about real-world objects. The IOD utilized to define an image is dependent upon the type and acquisition of the image. Within the DICOM Information Model, SOP classes define how to transmit images between two systems and IODs define the actual images. The DICOM Information Model defines a one-to-one relationship between storage SOP classes and their corresponding IODs. The combination of SOP classes and IODs allow accurate and consistent display of images between an acquisition device and image processing and analysis software, including the software of interest referred to herein.

Embodiments of the present invention include a computer-implemented method, a computer program product, and a computer system where program code executing on one or more processors verifies a software of interest for proper calculation of measurements related to a user-implemented annotation. In some examples, program code executing on one or more processors, monitors an imaging software utilized to analyze DICOM images and provides an accuracy check on certain aspects. For example, the program code can automatically launch an additional user interface (e.g., a window) on a graphical user interface and implement an annotation within the window. In some examples, the program code automatically implements the annotation (e.g., shape), but in some other examples, the program code launches the additional window which is a user interface that obtains an input of the annotation from a user. Based on the annotation (e.g., shape drawn on the image, either automatically or by the user), the program code calculates various values related to the image. The calculated details can include, but are not limited to, shape measurements (e.g., length and volume) and pixel statistics (e.g., mean and standard deviation pixel intensity). In some examples, the program code also calculates derived medical measurements such as standard uptake value (SUV), the ratio of the image derived radioactivity concentration and the whole body concentration of the injected radioactivity, for positron emission Tomography (PET) studies using the annotation characteristics and metadata associated with the PET studies.

In embodiments of the present invention, the calculations performed by the program code, based on automatically opening a window and annotating an image, are implemented with a goal of being accurate and producing a true measurement value. In software that manages DICOM images, goals can be performance-driven and accuracy and true measurement values can be sacrificed for speed and to cut processing overhead. Thus, aspects of embodiments of the present invention operate as checks and balances on existing DICOM display and annotation software. Embodiments of the present invention provide transparency into this software so that any programmatical decisions that adversely affect functionality to increase speed can be revealed and their impacts mitigated. As such, in embodiments of the present invention, the program code calculates values independent from the software of interest and by executing (e.g., all of) the calculations outlined in each measurement's definition. The program code utilizes precision data types and does not use any approximations or assumptions that would introduce error into the calculation.

Calculations in a software of interest can include various shortcuts to meet performance goals and to reduce processing costs. For example, in an example of a software of interest, which can be checked utilizing the aspects described herein, the software calculates a SUV scale factor for a single slice and uses this slice calculation for all 3D sphere calculations. The repetition of this same value across all these calculations creates discrepancies. Meanwhile, in embodiments of the present invention, the program code calculates a SUV scale factor on a per slice basis, avoiding the discrepancies. As will be discussed below, program code in embodiments of the present invention can identify this discrepancy and provide transparency to users. In another example, program code in embodiments of the present invention utilizes a larger number of voxels being checked for peak than the software of interest, and the program code of embodiments of the present invention utilizes a more exact edge pixel detection than the software of interest (see, FIG. 9). A voxel represents a value on a regular grid in three-dimensional space. These types of differences in calculation methods can add up, attributing to discrepancies between the software of interest and the program code in embodiments of the present invention.

Shortcuts that lead to discrepancies can be common in software because of performance and processing constraints. There can be a perceivable difference in speed between utilizing calculations in a software of interest and utilizing calculations in a specification document. In the 3D sphere calculation example, a software of interest, by determining a SUV scale factor for a single slice and using this slice calculation for all 3D sphere calculations provides a response in seconds or less for 3D sphere calculations. Meanwhile, in this example, the program code in embodiments of the present invention, because it prioritizes accuracy, even using multithreading on all available threads, and ~100% CPU utilization, takes ~10-60 seconds to calculate values associated with a small 3D sphere and ~5-10 minutes to calculate values associated with a larger (e.g., medium-sized) sphere.

Embodiments of the present invention are inextricably linked to computing and are directed to a practical application at least because the methods, systems, and computer program products described herein address an issue unique to computing, specifically to medical imaging analysis and processing software. As understood by one of skill in the art, DICOM images and medical images, in general, are extremely detailed and thus, rendering these images correctly and deriving data associated with the images, including utilizing aspects of the images and metadata associated with the images in calculations for clinical situations, is challenging based on the level of detail and density of data. For software related to medical imagery to be useful, the software is evaluated based on speed of operation because users need results quickly. Additionally, legacy equipment upon which the software of interest is executed can impose infrastructure constraints. The denseness of the data from which these results are derived and processing challenges can both hinder the speed at which results are available, so shortcuts can be implemented in the calculations in software solutions. Embodiments of the present invention provide a practical application because they automatically detect when these shortcuts create inaccuracies outside of a range that is acceptable for result utilization. Embodiments of the present invention are inextricably tied to computing because the issues addressed are unique to computing, specifically, digital image processing, and the solution is (necessarily) implemented within this realm (e.g., to practically address the issue). As will be described herein, program code in embodiments of the present invention launches an interface, automatically annotates a digital images, commences calculations based on a specification, and provides the user with the results, all within a user interface and by annotating a digital image through a user interface.

Embodiments of the present invention provide significantly more than existing approaches at least because they address an issue in these existing approaches. As described above, shortcuts implemented in image processing and analysis software, including medical image processing software, can introduce inaccuracies into the results provided to users. Embodiments of the present invention comprise an additional check on these results, increasing the accuracy of existing approaches. For example, program code in embodiments of the present invention checks functionality of existing image processing and analysis software, which includes functionality to display and annotate medical images. Program code in embodiments of the present invention launches a user interface (e.g., window) and automatically draws ROIs, and implement calculation in accordance with pre-defined specifications (e.g., of the product owner), which can be saved in a document and/or database and/or pre-defined industry best practices. Thus, the program code evaluates the accuracy of the calculations performed within the software of interest to determine whether the results within the software are acceptable based on the pre-defined specifications and/or the pre-defined industry best practices. If the program code determines the results are outside of an acceptable range (which can be pre-defined), the program code immediately alerts the user and/or automatically implements a mitigation action. Thus, embodiments of the present invention provide a verification that is not available in existing solutions, thus, provided significantly more. Advantages provided by aspects of embodiments of the present invention which will be discussed in greater detail herein can include but are not limited to: 1) quick automation workflow; 2) visibility of subpixel calculations and other results; and/or 3) generation of a report which shows measurement results as well as image captures.

Aspects of various embodiments of the present invention automatically implement annotations in medical images and provide users with a sanity check on calculations related to similar annotations implemented with a software of interest. In general, a software of interest related to medical imaging and analysis will provide a user with multiple forms of annotations to obtain quantitative data from a displayed image. Within a software of interest, each type of annotation provides a user with a different result set. An image's IOD defines how the software of interest translates dimensions in the displayed image to real world values with physical units. An image's DICOM object provides the data to transform the ROI from pixels to real-world values with physical units. Annotations utilized to derive quantitative values within the software of interest and as part of the sanity check implemented in embodiments of the present invention include, but are not limited to, a 2-point ROI (an annotation to determine several values contained within a planar region including area, perimeter, major axis length, minor axis length, maximum (radioactive) density, minimum (radioactive) density, mean, standard deviation (application to computed topography (CT) and PET images)). Annotations can also include a 3D sphere annotation which is an annotation to determine several values contained within a sphere where the number of images spanned by the annotation is dependent on the sphere's diameter and the slice thickness of the series as the series' DICOM object provides the data to transform the ROI from pixels to real-world values with physical units (e.g., diameter, volume, peak SUV (relevant only to PET images). Annotation can also include an angle annotation which measures an angle, in degrees, between two intersecting lines (different software of interest may determine a given angle from a number of points, including 3-4 points). Another possible annotation is area which determines the area within a planar region. Various annotations are referred to as circle and ellipse annotations, which determine several values contained within a circular or elliptical region (e.g., area, perimeter, major axis length, minor axis length, maximum density (applicable to CT and PET images), minimum density (applicable to CT and PET images), mean (applicable to CT and PET images), and standard deviation (applicable to CT and PET images)). Certain annotations are referred to as Cardiothoracic Ratio (CTR) annotations; a CTR 4-Point) measurement is used to measure the ratio (percentage) between the maximum horizontal cardiac diameter (length) and maximum horizontal thoracic diameter (length) and a CTR 6-Point measurement is used to measure the ratio (percentage) between the maximum horizontal cardiac diameter (length) and maximum horizontal thoracic diameter (length) with a sloped vertical axis. Additional annotations include density (quantifying an image transformation point), elliptical ROI (several values within a circular or elliptical region, including but not limited to area, perimeter, major axis length, minor axis length, maximum density, minimum density, mean, and standard deviation). A freehand ROI annotation determines several values in a planar region (e.g., area, perimeter, length, major axis length, minor axis length, maximum density, minimum density, mean standard deviation). The polygonal ROI annotation determines several values contained within a geometric region (e.g., area, perimeter, length, major axis length, minor axis length, maximum density, minimum density, mean standard deviation). The rectangular ROI annotation determines several values contained within a rectangular region (e.g., area, perimeter, maximum density, minimum density, mean, standard deviation). Other possible annotations are a ruler annotation which determines the length between two points using a distance formula, a slope annotation, which determines the slope between two points using a simple slope formula (e.g., velocity, length, time, gradient, velocity time integral (e.g., peak velocity, peak gradient, time), volume (area, biplane volume)).

Because embodiments of the present invention operate as a check on software of interest, in embodiments of the present invention, program code executing on one or more processors utilizes one or more of a software requirements specification (SRS), standard uptake value (SUV) pseudocode, and/or any user story requirements. An SRS is a document (e.g., file) that states how program code within software of interest should be calculating values, although some of the calculations may be defined by industry standards. PET images account for variations in the injection dose and patient size in order to provide quantitative imaging. A SUV compensates for these variations and may be correlated with the patient's body weight, lean body mass, body surface area, or ideal body weight within a software of interest. The correlations can utilize an image's patient's weight and patient's size, which can be provided in units of kilograms and centimeters.

Program code in embodiments of the present invention performs a verification and validation process to determine if design outputs correspond to design inputs. How a given value should be calculated within a software of interest can be defined by a combination of customized specification details, legacy values, and/or industry standard values. Discrepancies occur when shortcuts are implemented within a software of interest that do not produce the intended results. Program code in embodiments of the present invention checks calculations within a software of interest by determining how a given calculation should be performed and performing this calculation, independently from the software of interest. The specifications which the program code analyzes and automatically implements into calculations can include, but are not limited to, an SRS, a system design specification (SDS), and/or and legacy references. The program code obtains the specification for a calculation and an original DICOM image and determines whether the correspondence of design outputs to deign inputs is within an acceptable range. In some examples, this acceptable range is close to 100%. Calculations in which the program code can be utilized to evaluate determinations in software of interest include, but are not limited to, measurements for complex areas such as density, SUV, subpixel logics, and/or sphere.

FIG. 1 is a workflow 100 that illustrates various aspects of some embodiments of the present invention. The workflow 100 aspects are illustrated by FIGS. 2-6, which demonstrate the implementation of aspects of the workflow 100 from a perspective of a user viewing a user interface. The workflow 100 and these examples together illustrate program code in embodiments of the present invention launching a window, drawing annotation on a displayed (medical) image, obtaining the requirements for calculations based on the annotations, and processing the annotation based on the requirements. These requirements can be pre-defined by a software product owner.

Figure 5:
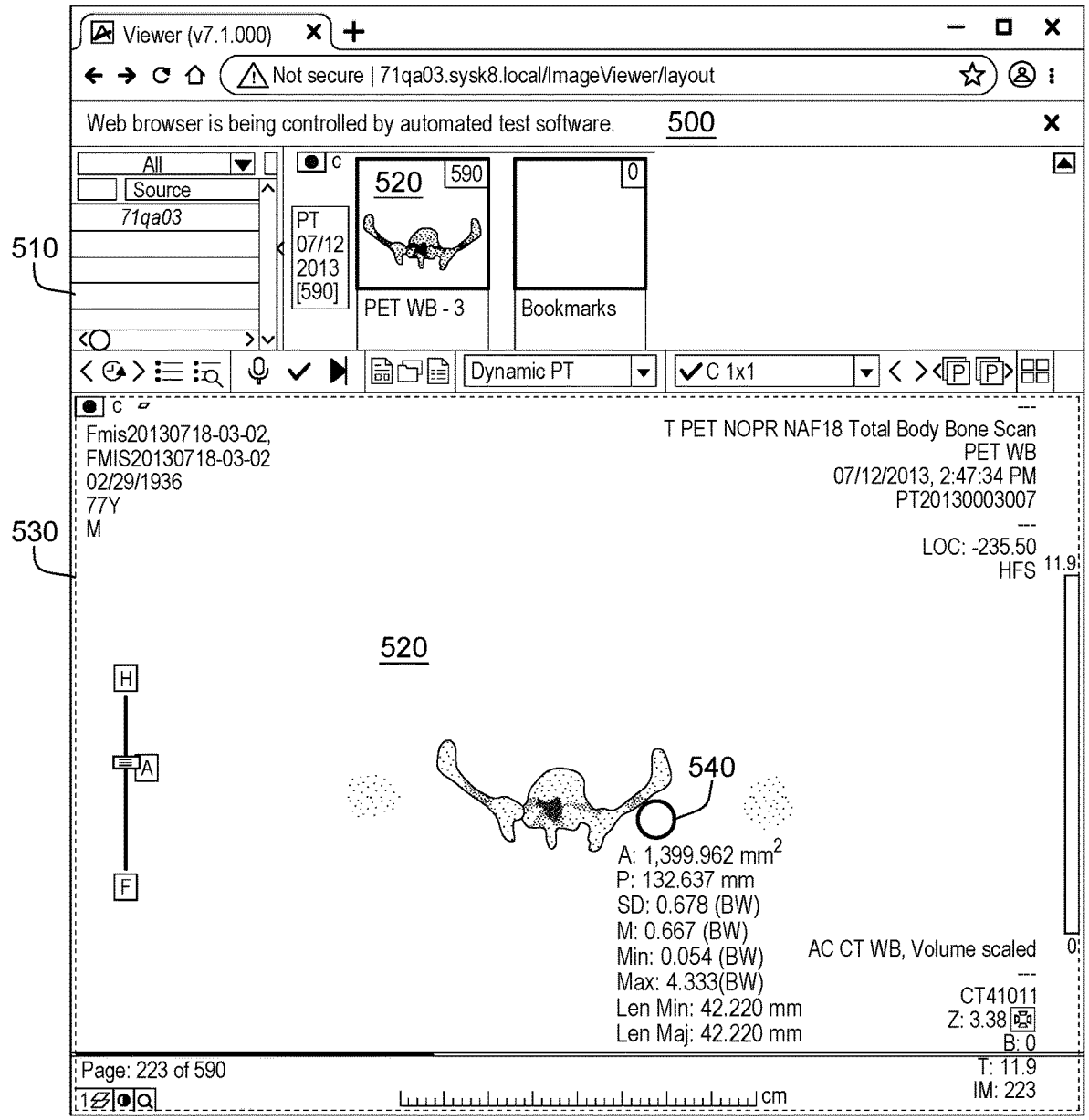
FIG. 5 depicts an example of a visual interface generated in various aspects of the present invention.
Figure 6:
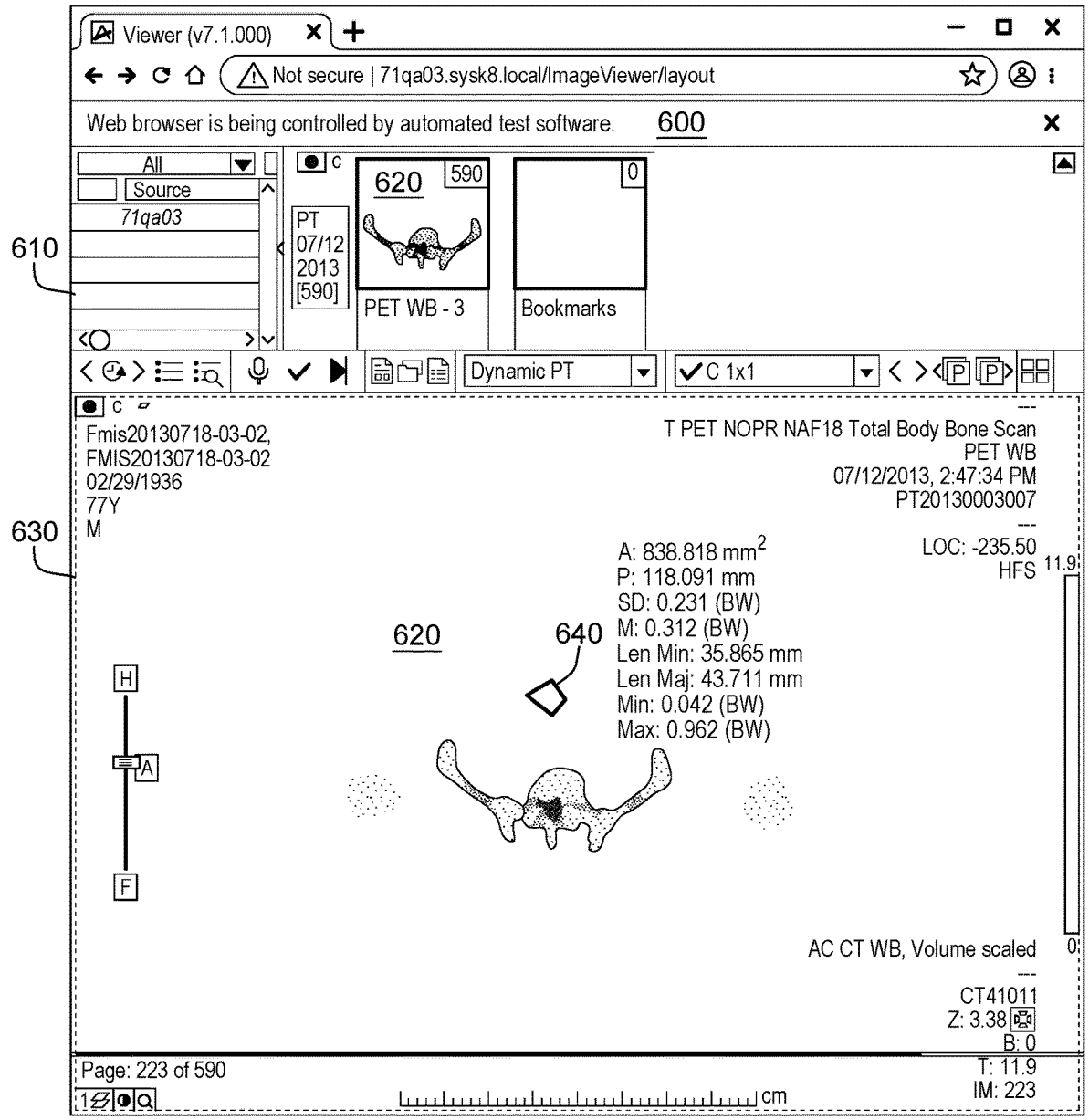
FIG. 6 depicts an example of a visual interface generated in various aspects of the present invention.
Figure 7:
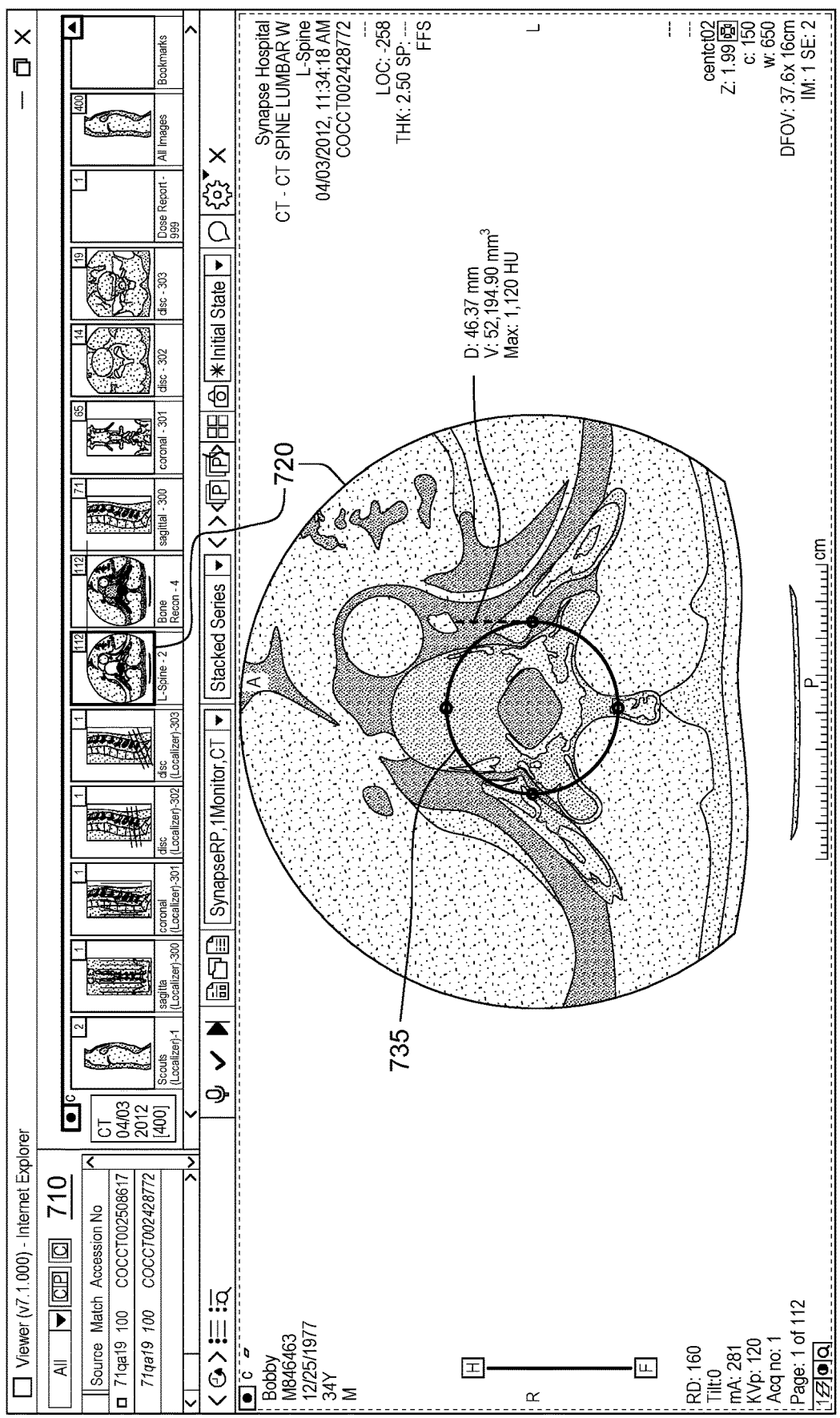
FIG. 7 is an example a viewer of a software of interest displaying an image, as well as an annotation of the image, within the viewer in accordance with various aspects of the present invention.

FIGS. 2-6 includes examples of a desktops 200, 300, 400, 500, 600 of a user. The desktop 200, 300, 400, 500 includes a user interface, a viewer 210, 310, 410, 510, 610 of a software of interest displaying an image 220, 320, 420, 520, 620. FIG. 7 is another example a viewer 710 of a software of interest displaying an image 720, as well as an annotation 735 of the image 720, within the viewer 710. This annotation is not automatically implemented by the program code in embodiments of the present invention.

Referring to FIG. 1, the program code of an example herein, executed by one or more processors, determines that the image 220, 320, 420, 520, 620 has been selected in the software of interest and is displayed in the viewer 210, 310, 410, 510, 610 (110). The program code automatically opens a window 230, 330, 430, 530, 630 (separate from the viewer 210, 310, 410, 510, 610 for visual contrast) and displays the image 220, 320, 420, 520, 620 in the window 230, 330, 430, 530, 630 (120).

Figure 2:
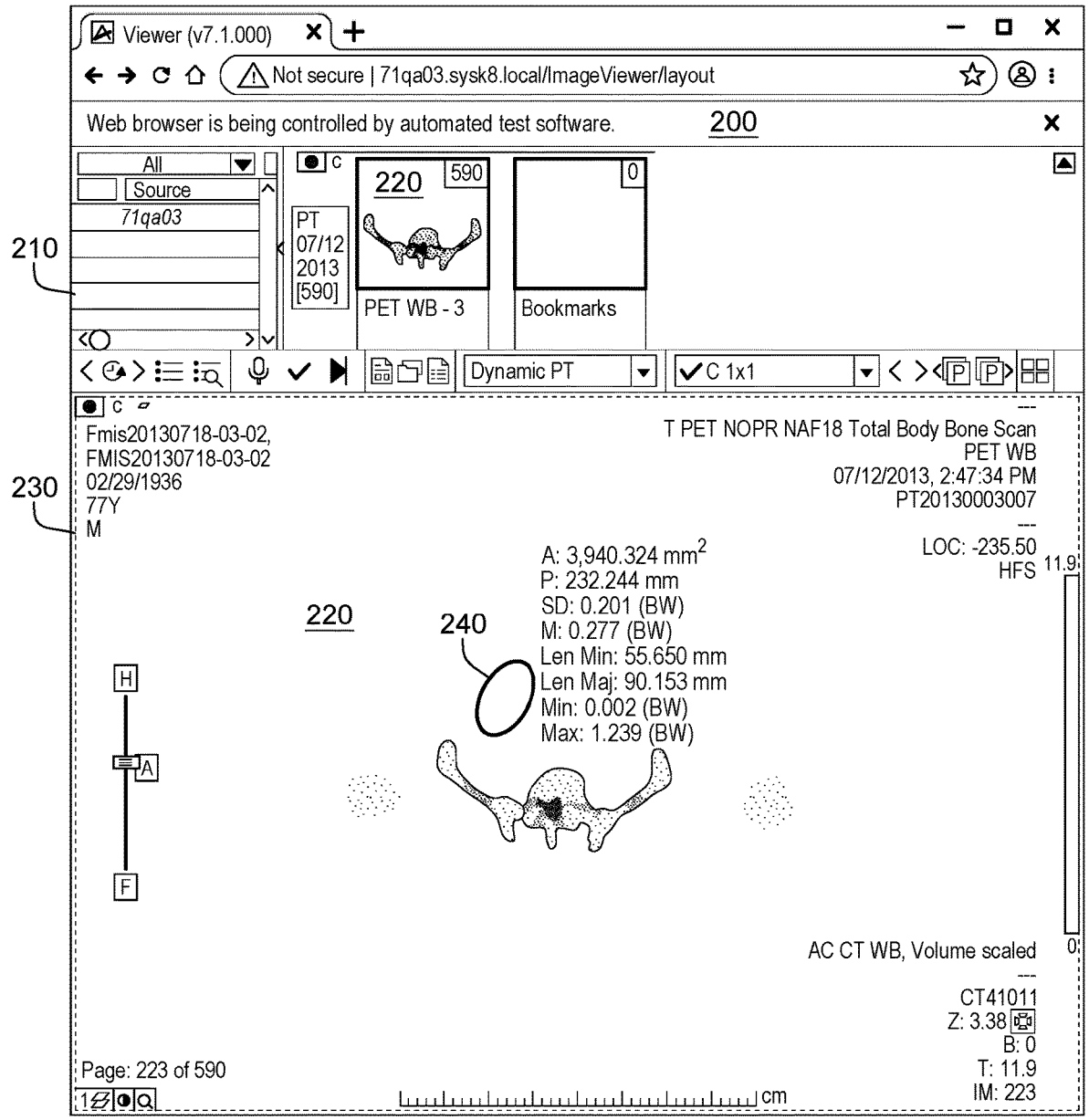
FIG. 2 depicts an example of a visual interface generated in various aspects of the present invention.
Figure 3:
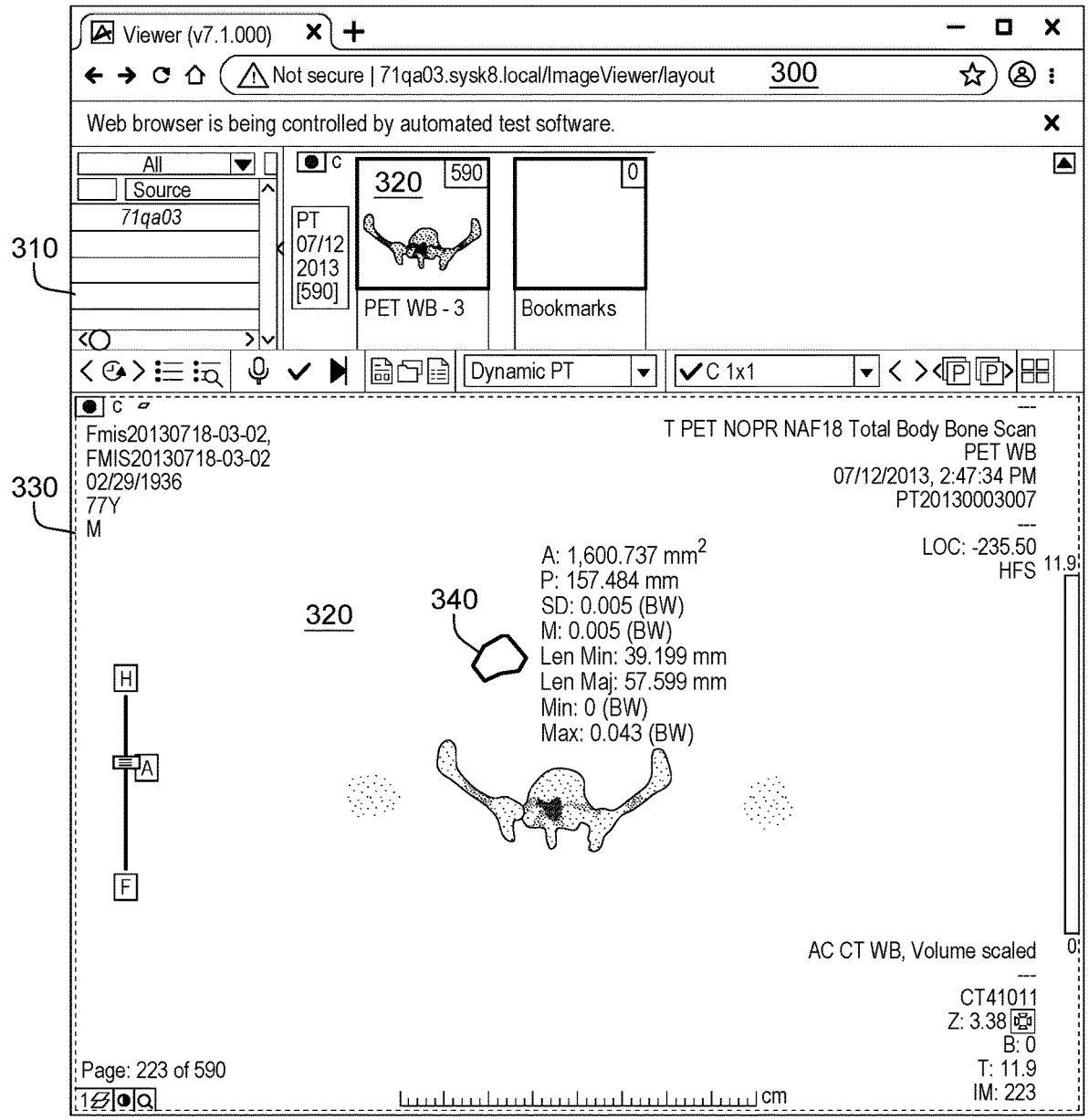
FIG. 3 depicts an example of a visual interface generated in various aspects of the present invention.
Figure 4:
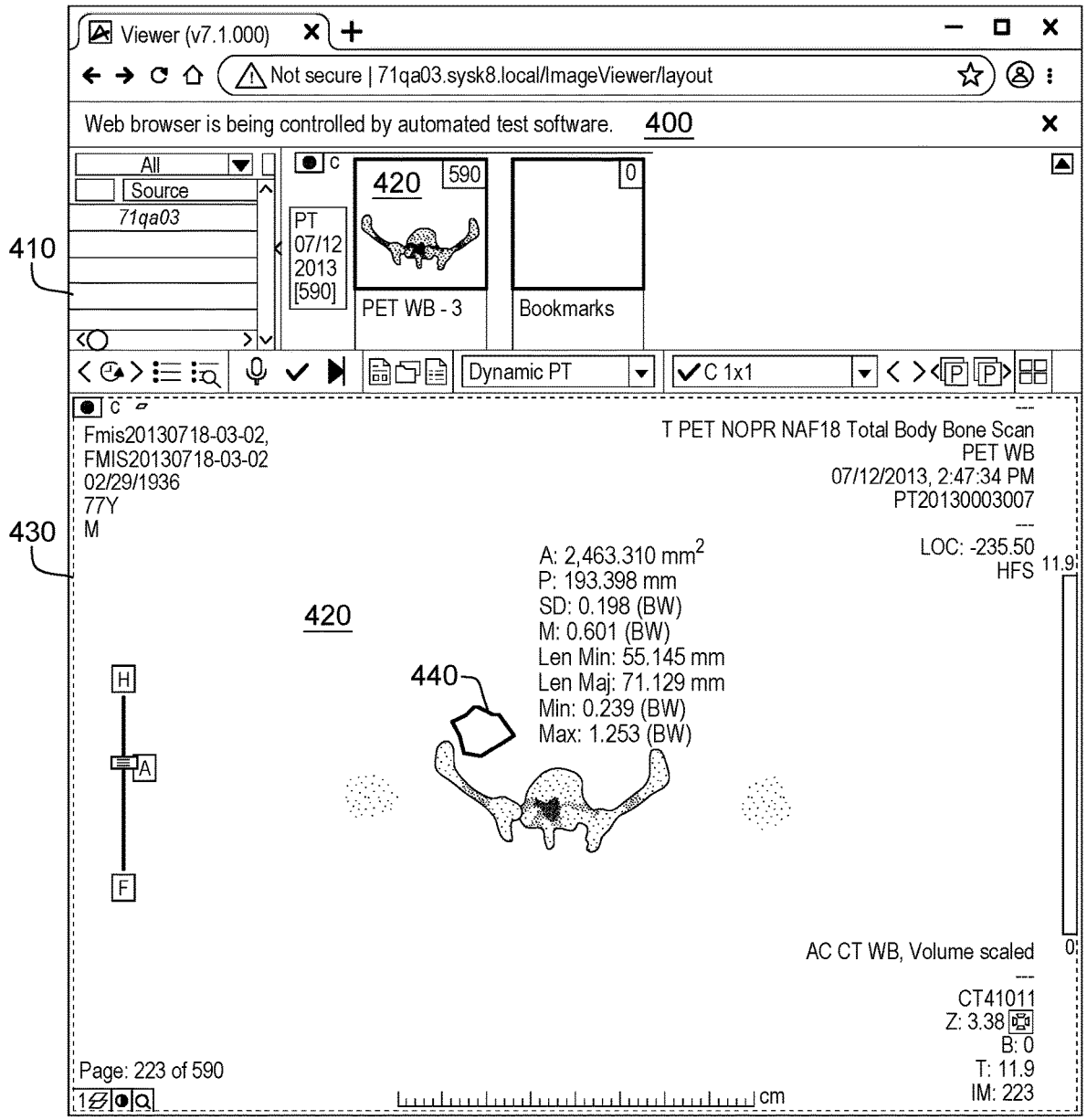
FIG. 4 depicts an example of a visual interface generated in various aspects of the present invention.

The program code automatically annotates a region of the image 220, 320, 420, 520 in the window 230, 330, 430, 530, 630 (130). The program code obtains equations, formulas, logic, etc., for calculating values associated with the annotation (e.g., from a specification), determines how to make the calculation, and implements the calculations separately from the software of interest (140). In FIG. 2, the program code annotates the image using an ellipse annotation 240. In FIGS. 3-4, the program code annotates the image using a 2-point ROI annotation 340, 440. In FIG. 5, the program code annotates the image using a circle annotation 540. In FIG. 6, the program code annotates the image using a freehand annotation 640. In this example, the image 120 is a PET image and the annotation is an ellipse 140. Based on implementing the ellipse and circle annotations, the program code calculates values including area, perimeter, standard deviation, mean, minor axis length, and major axis length. Based on implementing the 2-pt ROI annotations, the program code calculates values including area, perimeter, standard deviation, mean, minor axis length, major axis length, minimum (radioactive) density, and maximum (radioactive) density. In some examples, the program code will redraw a 2-pt ROI annotation automatically if the original implementation does not include enough voxels in an area of interest on the image. Based in implementing the freehand annotation, the program code calculates values including area, perimeter, standard deviation, mean, minor axis length, and major axis length.

Returning to FIG. 1, the program code obtains the values calculated for the same annotation by the software of interest and compares the independently calculated values with the software of interest (150) to identify discrepancies between the values (160). In some examples, the program code automatically saves the automatically annotated image and the calculations.

Aspects of the present invention can be implemented as a quality assurance test for a software product. By comparing calculations utilizing a specification to calculations in the software of interest, the program code can isolate shortcuts taken in the software to improve performance which have impacted calculation accuracy. For example, in one version of a given software of interest, because SUV calculations are all done, per the specification, on a per slice basis to have the highest precision possible, the software, based on performance limitations related to processing, utilized SUV factors from a first image slice, only. The program code determined that this shortcut adversely affected the data returned by the software. The program code uncovered this issue by being implemented as an automated test and cycling through evaluating various SUV measurements. Upon integration of a fix in the software of interest, an example of aspects of the present invention can be utilized to verify that the fix addresses the issue, for example, by re-testing specific SUV cases (e.g., +/−50 cases).

In some embodiments of the present invention, the program code evaluates the veracity of the software of interest utilizing test data. The test data can include patterned images which are generated by the program code. In some examples, the program code utilizes Pydicom which is a pure Python module for parsing DICOM files, to create clear images with known pixel values and evenly spaced regions for use in testing the software. To test the software of interest, the program code evaluates unique images for each requirement area. For example, the program code can generate test case data for each SRS The test case data for each SRS (or otherwise defined requirement) can include, but is not limited to: 1) a patterned image with attributes that satisfy the specific requirement; 2) a GSPS (grayscale softcopy presentation state storage) file for the image; and 3) a set of expected values derived by the program code of the present invention that cover all annotation measurement from the GSPS file. In some examples, the program code traces annotations from these GSPS files can be manually traced to increase accuracy.

Figure 8:
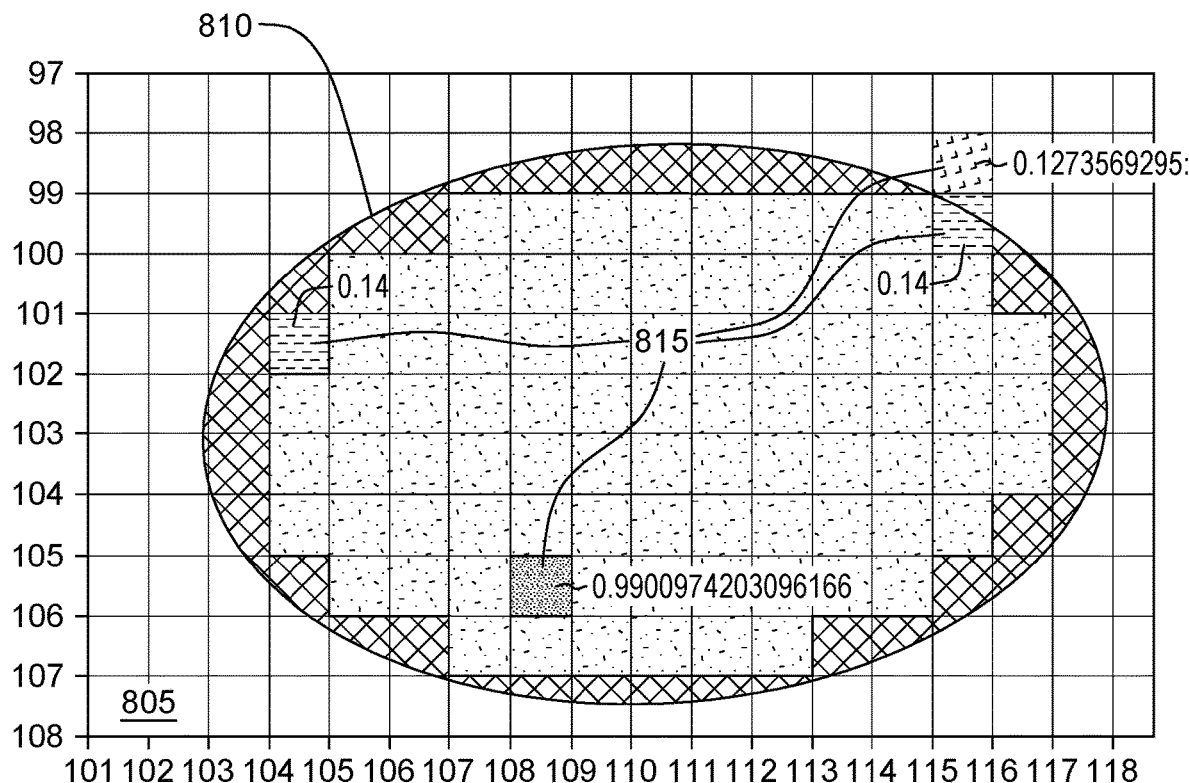
FIG. 8 depicts an example of a comparison by the program code of values calculated in software of interest, related to an annotated region (an ellipse, in this example), and when calculated by the program code from the specification.

Returning to FIG. 1, if the program code determines that there is a discrepancy between values, the program code determines the reason for the discrepancy (170). For example, the program code can determine if there is an edge pixel case, or a rounding error. FIG. 8 is an example of a comparison by the program code of values calculated in software of interest, related to an annotated region (an ellipse, in this example), and when calculated by the program code from the specification. In determining whether there is a discrepancy (FIG. 1, 160), the program code in embodiments of the present invention determines whether software passes a test, fails a test, and/or fails, but the discrepancies are within a pre-defined tolerance. Based on determining that there is a discrepancy, the program code automatically reruns the annotation and associated calculations with a graphical interface to visually confirm that this is an error due to higher precision by the program code (180). FIG. 8 is an example 800 that illustrates an annotated region 810 of a medical image 805 where certain of the pixels 815 were evaluated differently in the software than by the program code, creating discrepancies. The results for the ellipse annotation 825 show a specific discrepancy between the program code and the software of interest in calculating a minimum density. The result calculated by the program code is listed first, followed by the result calculated by the software of interest.

Figure 9:
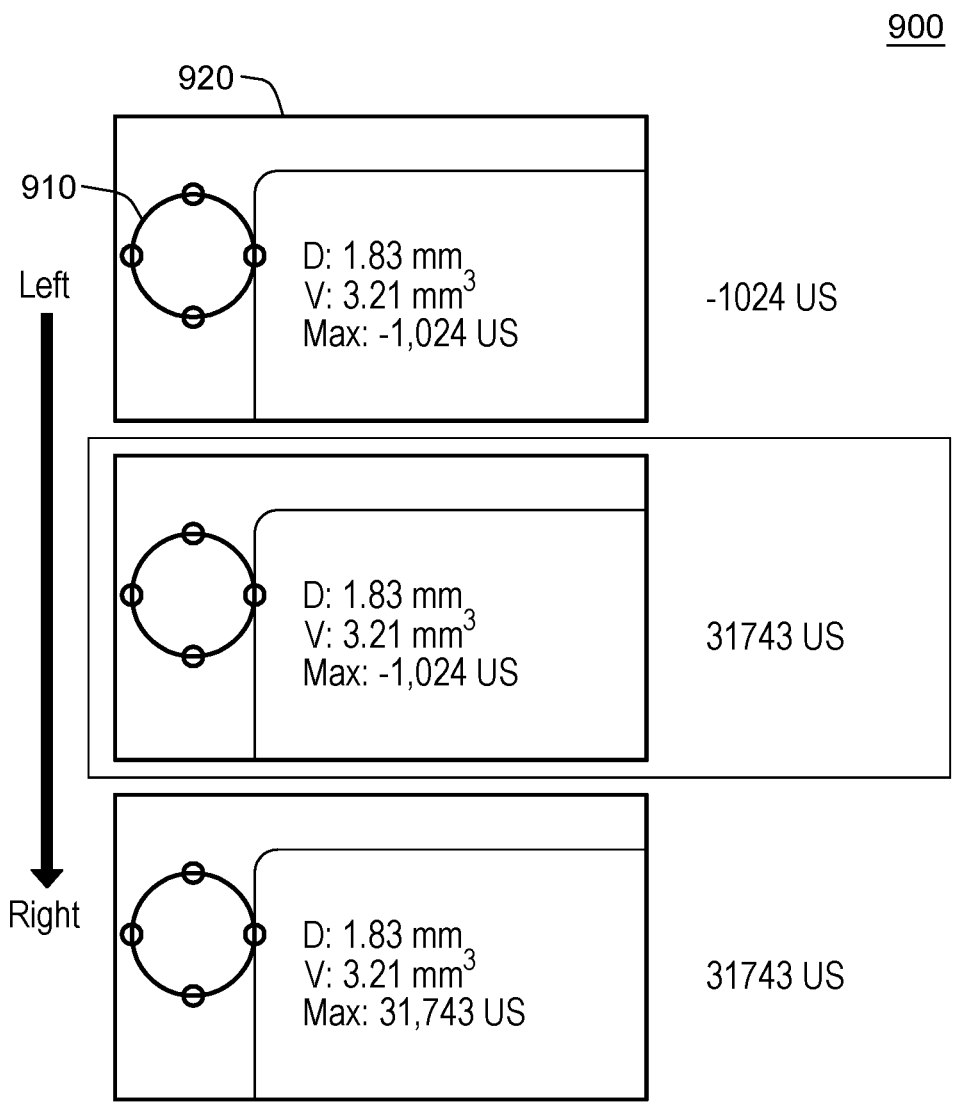
FIG. 9 is a simplified example that illustrates program code in an example herein detecting an error in a calculation in a software of interest.

FIG. 9 is a simplified example 900 that illustrates program code in an example herein detecting an error in a calculation in a software of interest. Specifically, in this example 900, the program code detects voxels that the software of interest did not detect in a 3D sphere where a circular annotation 910 was automatically implemented by the program code. The example illustrates diameter, volume, and maximum SUV. Moving from left to right on a medical image 920. In this example 900, the program code detects voxels that the software did not detect. As discussed in FIG. 1, the program code obtains a method of calculation from a specification and thus independently calculates aspects related to each annotation it implements. In this example, the program code calculates diameter, volume, max SUV, and peak SUV, according to an SRS The program code performs full calculations without approximations. As the calculations are involved, in some examples, the program code is implemented in a manner that enables multi-threading. Meanwhile, the software of interest performs the calculation using subpixel logic. The program code also applies SUV per slice, as defined by DICOM.

Embodiments of the present invention include a computer-implemented method, a computer program product, and a system where program code, executed on one or more processors, determines that an image has been selected in a software of interest and is displayed in a viewer of the software of interest, where the viewer is a graphical user interface of the software of interest in a screen communicatively coupled to the one or more processors. The program code automatically launches a graphical user interface comprising a window, on the screen, where the window is displayed on the screen contemporaneously with the viewer. The program code automatically annotates a region of the image in the window, where the annotating comprises an annotation defined by a specification document stored on a memory communicatively coupled to the one or more processors. The program code obtains, from the specification, instructions for calculating a set first of the one or more values based on the annotation defined by the specification. The program code calculates, based on the instructions, the first set of the one or more values. The program code obtains, from the software of interest, a second set of the one or more values, where the second set of the one or more values were calculated by the software of interest based on the annotation. The program code compares the first set of the one or more values to the second set of the one or more values to identify one or more discrepancies outside of a pre-defined tolerance. Based on identifying one or more discrepancies outside of the pre-defined tolerance, the program code determines a reason for each discrepancy of the one or more discrepancies, the determining comprises displaying the reason for each discrepancy in the window.

In some examples, the program code initiates an action to address at least one of the one or more discrepancies.

In some examples, the program code clears the annotation in the window.

In some examples, the program code automatically re-annotates the region of the image in the window. The re-annotating comprises visually confirming the reason for each discrepancy in the window.

In some examples, the reason is that the calculating, based on the instructions, is of a higher precision than calculating by the software of interest.

In some examples, the reason is selected from the group consisting of: an edge pixel case and a rounding error.

In some examples, the program code automatically launching the window comprises the program code positioning the window in a position on the screen such that it does not overlap the viewer.

In some examples, the image comprises a Digital Imaging and Communications in Medicine (DICOM) image.

In some examples, the values are selected from the group consisting of: diameter, volume, peak standard uptake value (SUV), maximum SUV, area, perimeter, major axis length, minor axis length, maximum density, minimum density, mean, and standard deviation.

In some examples, the annotation defined by the specification document is selected from the group consisting of: ellipse, circle, 2-point ROI, freehand, sphere, and rectangle.

In some examples, the program code generates the image and generating the image comprises creating the image with known pixel values and evenly spaced regions.

Figure 10:
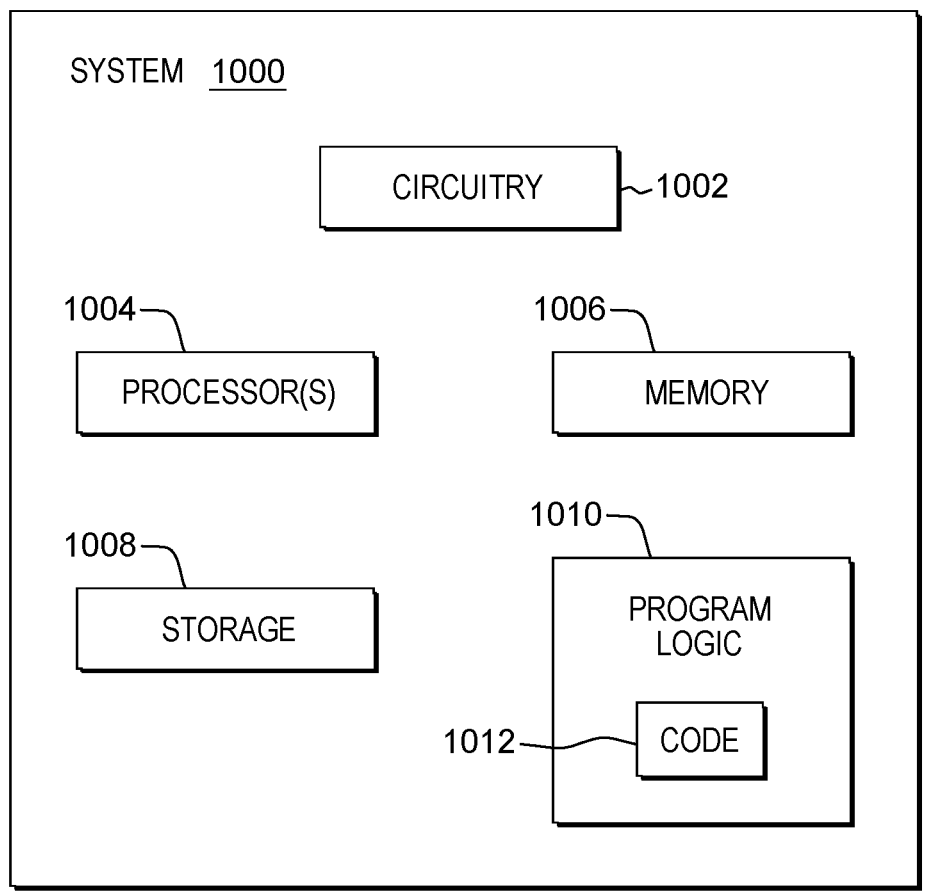
FIG. 10 illustrates a block diagram of a resource in computer system, which is part of the technical architecture of certain embodiments of the technique.

FIG. 10 illustrates a block diagram of a resource 1000 in computer system, which is part of the technical architecture of certain embodiments of the technique. The resource can include a computing device upon which the software and/or the program code are executed. The resource 1000 may include a circuitry 1002 that may in certain embodiments include a microprocessor 1004. The computer system 1000 may also include a memory 1006 (e.g., a volatile memory device), and storage 1008. The storage 1008 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 1008 may comprise an internal storage device, an attached storage device and/or a network accessible storage device. The system 1000 may include a program logic 1010 including code 1012 that may be loaded into the memory 1006 and executed by the microprocessor 1004 or circuitry 1002.

In certain embodiments, the program logic 1010 including code 1012 may be stored in the storage 1008, or memory 1006. In certain other embodiments, the program logic 1010 may be implemented in the circuitry 1002. Therefore, while FIG. 10 shows the program logic 1010 separately from the other elements, the program logic 1010 may be implemented in the memory 1006 and/or the circuitry 1002. The program logic 1010 may include the program code discussed in this disclosure that facilitates the reconfiguration of elements of various computer networks, including those in various figures.

Figure 11:
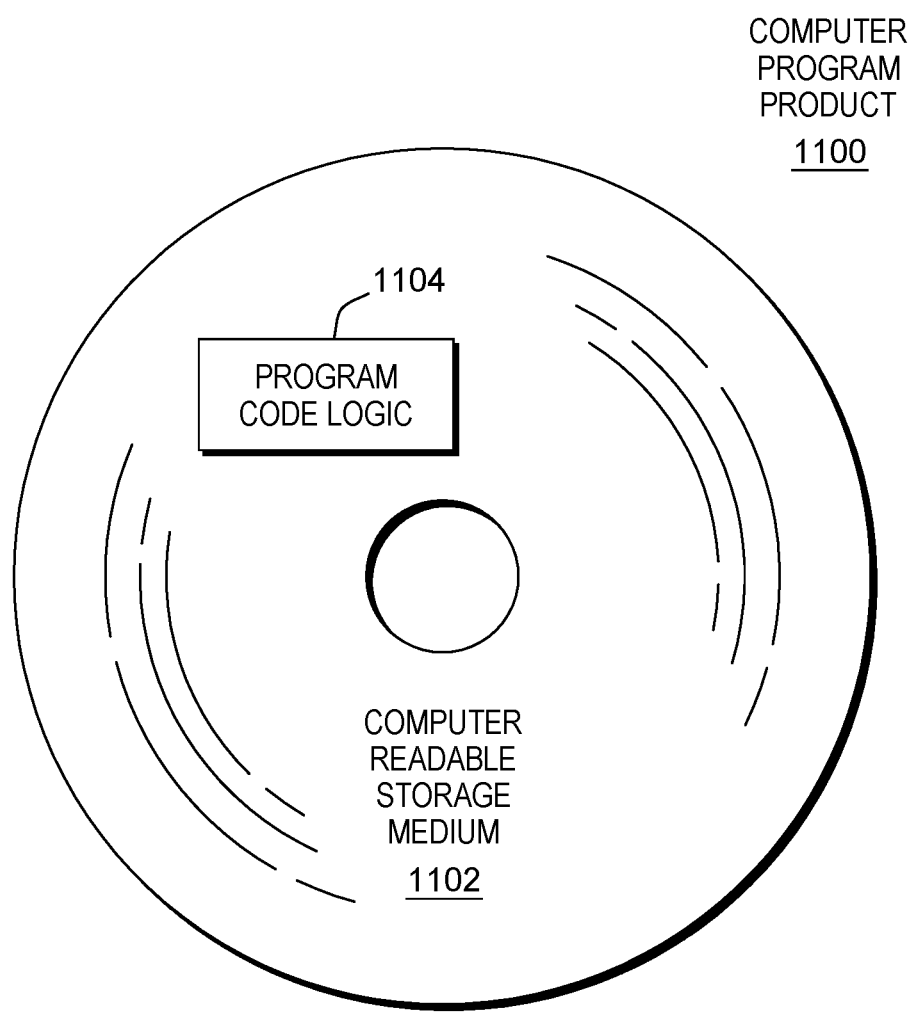
FIG. 11 depicts a computer program product incorporating one or more aspects of the present invention.

Using the processing resources of a resource 1000 to execute software, computer-readable code or instructions, does not limit where this code can be stored. Referring to FIG. 11, in one example, a computer program product 1100 includes, for instance, one or more non-transitory computer readable storage media 1102 to store computer readable program code means or logic 1104 thereon to provide and facilitate one or more aspects of the technique.

As will be appreciated by one skilled in the art, aspects of the technique may be embodied as a system, method or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, aspects of the technique may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electro-magnetic, optical or any suitable combination thereof. A computer readable signal medium may be any computer readable medium that is not a computer readable storage medium and that can communicate, propagate, or transport a program for use by or in connection with an instruction execution system, apparatus, or device. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electro-magnetic, optical or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the technique may be written in any combination of one or more programming languages, including an object-oriented programming language, such as Java, Smalltalk, C++ or the like, and conventional procedural programming languages, such as the "C" programming language, PHP, ASP, assembler or similar programming languages, as well as functional programming languages and languages for technical computing (e.g., Python, Matlab). The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). Furthermore, more than one computer can be used for implementing the program code, including, but not limited to, one or more resources in a cloud computing environment.

Aspects of the technique are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions, also referred to as software and/or program code, may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the technique. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the above, one or more aspects of the technique may be provided, offered, deployed, managed, serviced, etc. by a service provider who offers management of customer environments. For instance, the service provider can create, maintain, support, etc. computer code and/or a computer infrastructure that performs one or more aspects of the technique for one or more customers. In return, the service provider may receive payment from the customer under a subscription and/or fee agreement, as examples. Additionally, or alternatively, the service provider may receive payment from the sale of advertising content to one or more third parties.

In one aspect of the technique, an application may be deployed for performing one or more aspects of the technique. As one example, the deploying of an application comprises providing computer infrastructure operable to perform one or more aspects of the technique.

As a further aspect of the technique, a computing infrastructure may be deployed comprising integrating computer readable code into a computing system, in which the code in combination with the computing system is capable of performing one or more aspects of the technique.

As yet a further aspect of the technique, a process for integrating computing infrastructure comprising integrating computer readable code into a computer system may be provided. The computer system comprises a computer readable medium, in which the computer medium comprises one or more aspects of the technique. The code in combination with the computer system is capable of performing one or more aspects of the technique.

Further, other types of computing environments can benefit from one or more aspects of the technique. As an example, an environment may include an emulator (e.g., software or other emulation mechanisms), in which a particular architecture (including, for instance, instruction execution, architected functions, such as address translation, and architected registers) or a subset thereof is emulated (e.g., on a native computer system having a processor and memory). In such an environment, one or more emulation functions of the emulator can implement one or more aspects of the technique, even though a computer executing the emulator may have a different architecture than the capabilities being emulated. As one example, in emulation mode, the specific instruction or operation being emulated is decoded, and an appropriate emulation function is built to implement the individual instruction or operation.

In an emulation environment, a host computer includes, for instance, a memory to store instructions and data; an instruction fetch unit to fetch instructions from memory and to optionally, provide local buffering for the fetched instruction; an instruction decode unit to receive the fetched instructions and to determine the type of instructions that have been fetched; and an instruction execution unit to execute the instructions. Execution may include loading data into a register from memory; storing data back to memory from a register; or performing some type of arithmetic or logical operation, as determined by the decode unit. In one example, each unit is implemented in software. For instance, the operations being performed by the units are implemented as one or more subroutines within emulator software.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or steps plus function elements in the descriptions below, if any, are intended to include any structure, material, or act for performing the function in combination with other elements as specifically noted. The description of the technique has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular uses contemplated.

What is claimed is:

1. A computer-implemented method comprising:
   determining, by one or more processors, that an image has been selected in a software of interest and is displayed in a viewer of the software of interest, wherein the viewer is a graphical user interface of the software of interest in a screen communicatively coupled to the one or more processors;
   automatically launching, by the one or more processors, a graphical user interface comprising a window, on the screen, wherein the window is displayed on the screen contemporaneously with the viewer, wherein the selected image is displayed in the window;
   automatically annotating, by the one or more processors, a region of the selected image in the window, wherein the annotating comprises an annotation defined by a specification document stored on a memory communicatively coupled to the one or more processors;
   obtaining, by the one or more processors, from the specification document, instructions for calculating a first set of one or more values based on the annotation defined by the specification document;
   calculating, by the one or more processors, based on the instructions, the first set of the one or more values;
   obtaining, by the one or more processors, from the software of interest, a second set of the one or more values, wherein the second set of the one or more values were calculated by the software of interest based on the annotation;
   comparing, by the one or more processors, the first set of the one or more values to the second set of the one or more values to identify one or more discrepancies outside of a pre-defined tolerance between the first set of the one or more values and the second set of the one or more values; and
   based on identifying one or more discrepancies outside of the pre-defined tolerance, wherein each discrepancy is caused by a calculation error in the software of interest, determining, by the one or more processors, a reason for each discrepancy of the one or more discrepancies, wherein the determining comprises displaying the reason for each discrepancy in the window, wherein the reason is an issue in the calculation of the software of interest.

2. The computer-implemented method of claim 1, further comprising:
   initiating, by the one or more processors, an action to address at least one of the one or more discrepancies.

3. The computer-implemented method of claim 2, further comprising:
   clearing, by the one or more processors, the annotation in the window; and
   automatically re-annotating, by the one or more processors, the region of the selected image in the window, wherein the re-annotating comprises visually confirming the reason for each discrepancy in the window.

4. The computer-implemented method of claim 1, wherein the reason is that the calculating, based on the instructions, is of a higher precision than calculating by the software of interest.

5. The computer-implemented method of claim 1, wherein the reason is selected from the group consisting of: an edge pixel case and a rounding error.

6. The computer-implemented method of claim 1, wherein the automatically launching the window comprises positioning the window in a position on the screen such that it does not overlap the viewer.

7. The computer-implemented method of claim 1, wherein the image comprises a Digital Imaging and Communications in Medicine (DICOM) image.

8. The computer-implemented method of claim 1, where the values are selected from the group consisting of: diameter, volume, peak standard uptake value (SUV), maximum SUV, area, perimeter, major axis length, minor axis length, maximum density, minimum density, mean, and standard deviation.

9. The computer-implemented method of claim 1, wherein the annotation defined by the specification document is selected from the group consisting of: ellipse, circle, 2-point ROI, freehand, sphere, and rectangle.

10. The computer-implemented method of claim 1, further comprising:
generating, by the one or more processors, the selected image, wherein generating the selected image comprises creating the image with known pixel values and evenly spaced regions.

11. A system comprising:
a memory;
one or more processors in communication with the memory; and
program instructions stored on the memory that when executed by the one or more processors cause the one or more processors to execute a method comprising:
determining, by the one or more processors, that an image has been selected in a software of interest and is displayed in a viewer of the software of interest, wherein the viewer is a graphical user interface of the software of interest in a screen communicatively coupled to the one or more processors;
automatically launching, by the one or more processors, a graphical user interface comprising a window, on the screen, wherein the window is displayed on the screen contemporaneously with the viewer, wherein the selected image is displayed in the window;
automatically annotating, by the one or more processors, a region of the selected image in the window, wherein the annotating comprises an annotation defined by a specification document stored on a memory communicatively coupled to the one or more processors;
obtaining, by the one or more processors, from the specification document, instructions for calculating a first set of one or more values based on the annotation defined by the specification document;
calculating, by the one or more processors, based on the instructions, the first set of the one or more values;
obtaining, by the one or more processors, from the software of interest, a second set of the one or more values, wherein the second set of the one or more values were calculated by the software of interest based on the annotation;
comparing, by the one or more processors, the first set of the one or more values to the second set of the one or more values to identify one or more discrepancies outside of a pre-defined tolerance between the first set of the one or more values and the second set of the one or more values; and based on identifying one or more discrepancies outside of the pre-defined tolerance, wherein each discrepancy is caused by a calculation error in the software of interest, determining, by the one or more processors, a reason for each discrepancy of the one or more discrepancies, wherein the determining comprises displaying the reason for each discrepancy in the window, wherein the reason is an issue in the calculation of the software of interest.

12. The system of claim 11, further comprising:
initiating, by the one or more processors, an action to address at least one of the one or more discrepancies.

13. The system of claim 12, further comprising:
clearing, by the one or more processors, the annotation in the window; and
automatically re-annotating, by the one or more processors, the region of the selected image in the window, wherein the re-annotating comprises visually confirming the reason for each discrepancy in the window.

14. The system of claim 11, wherein the reason is that the calculating, based on the instructions, is of a higher precision than calculating by the software of interest.

15. The system of claim 11, wherein the reason is selected from the group consisting of: an edge pixel case and a rounding error.

16. The system of claim 11, wherein the automatically launching the window comprises positioning the window in a position on the screen such that it does not overlap the viewer.

17. The system of claim 11, wherein the image comprises a Digital Imaging and Communications in Medicine (DICOM) image.

18. The system of claim 11, where the values are selected from the group consisting of: diameter, volume, peak standard uptake value (SUV), maximum SUV, area, perimeter, major axis length, minor axis length, maximum density, minimum density, mean, and standard deviation.

19. A computer program product comprising:
a computer readable storage medium readable by one or more processors, the computer readable storage media storing instructions that when executed by the one or more processors the one or more processors execute a method comprising:
obtaining, from an ultrasound machine including a clinical display, wherein the ultrasound machine is communicatively coupled to the one or more processors, ultrasound data including images;
utilizing a neural network configured on the computing device to provide an inference and a confidence level for each image of the images;
displaying, on a display of the computing device, concurrently with a display of each image on the clinical display, each image of the images and the inference and the confidence level for each image of the images;
obtaining, via an interface of the computing device, during the displaying of a given image, an input; and
transmitting, via the communication link, to the ultrasound machine, the input, wherein the ultrasound machine effects a change based on obtaining the input, wherein the change is selected from the group consisting of: a visual change to a display of the given image on the clinical display and a change to a setting of an ultrasound probe communicatively coupled to the ultrasound machine;
determining, by the one or more processors, that an image has been selected in a software of interest and is displayed in a viewer of the software of interest, wherein the viewer is a graphical user interface of the software of interest in a screen communicatively coupled to the one or more processors;

automatically launching, by the one or more processors, a graphical user interface comprising a window, on the screen, wherein the window is displayed on the screen contemporaneously with the viewer, wherein the selected image is displayed in the window;

automatically annotating, by the one or more processors, a region of the selected image in the window, wherein the annotating comprises an annotation defined by a specification document stored on a memory communicatively coupled to the one or more processors;

obtaining, by the one or more processors, from the specification document, instructions for calculating a first set of one or more values based on the annotation defined by the specification document;

calculating, by the one or more processors, based on the instructions, the first set of the one or more values;

obtaining, by the one or more processors, from the software of interest, a second set of the one or more values, wherein the second set of the one or more values were calculated by the software of interest based on the annotation;

comparing, by the one or more processors, the first set of the one or more values to the second set of the one or more values to identify one or more discrepancies outside of a pre-defined tolerance between the first set of the one or more values and the second set of the one or more values; and based on identifying one or more discrepancies outside of the pre-defined tolerance, wherein each discrepancy is caused by a calculation error in the software of interest, determining, by the one or more processors, a reason for each discrepancy of the one or more discrepancies, wherein the determining comprises displaying the reason for each discrepancy in the window, wherein the reason is an issue in the calculation of the software of interest.

20. The computer program product of claim 19, further comprising:

initiating, by the one or more processors, an action to address at least one of the one or more discrepancies.

* * * * *